United States Patent
Herbst et al.

[11] Patent Number: 6,022,337
[45] Date of Patent: Feb. 8, 2000

[54] DENTAL ANESTHETIC AND DELIVERY INJECTION UNIT

[76] Inventors: Walter Herbst, 1875 N. Pond La., Lake Forest, Ill. 60045; Chris Quatrochi, 3856 N. Clark, Apt. 1B, Chicago, Ill. 60613; Michael Reiter, 829 N. Cuyler Ave., Oak Park, Ill. 60302

[21] Appl. No.: 09/028,009

[22] Filed: Feb. 23, 1998

Related U.S. Application Data

[60] Provisional application No. 60/057,531, Sep. 4, 1997.

[51] Int. Cl.[7] .................................................. A61M 37/00
[52] U.S. Cl. ........................................................ 604/131
[58] Field of Search ................................... 604/131, 151, 604/152, 232; 433/80

[56] References Cited

U.S. PATENT DOCUMENTS

| | | | |
|---|---|---|---|
| 4,755,172 | 7/1988 | Baldwin | 604/131 |
| 4,787,893 | 11/1988 | Villette | 604/188 |
| 4,936,833 | 6/1990 | Sams | 604/232 |
| 5,106,374 | 4/1992 | Apperson et al. | 604/131 |
| 5,244,463 | 9/1993 | Cordner et al. | 604/131 |
| 5,254,096 | 10/1993 | Rondelet et al. | 604/152 |
| 5,269,762 | 12/1993 | Armbruster et al. | 604/131 |
| 5,383,858 | 1/1995 | Reilly et al. | 604/131 |
| 5,423,747 | 6/1995 | Amano | 604/131 |
| 5,720,728 | 2/1998 | Ford | 604/131 |
| 5,741,227 | 4/1998 | Sealfon | 604/151 |

FOREIGN PATENT DOCUMENTS 094014488  7/1994  WIPO ................................. 604/131

*Primary Examiner*—Jeffrey A. Smith
*Assistant Examiner*—Eduardo C. Robert

[57] ABSTRACT

An improved injection device includes containing a pump and pump control circuitry, a handle with a needle for delivering a therapeutic agent to a patient, a cartridge holding the agent and a tube for delivering the agent from the cartridge to the handle. Preferably the cartridge is disposed in a cartridge holder coupled to the tube. A quick disconnect coupling is provided between the cartridge holder and the housing so that it can be easily mounted thereon. The housing further has a receptacle for receiving and storing the tip of the handle.

37 Claims, 8 Drawing Sheets

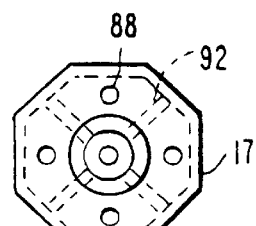
FIG.6A
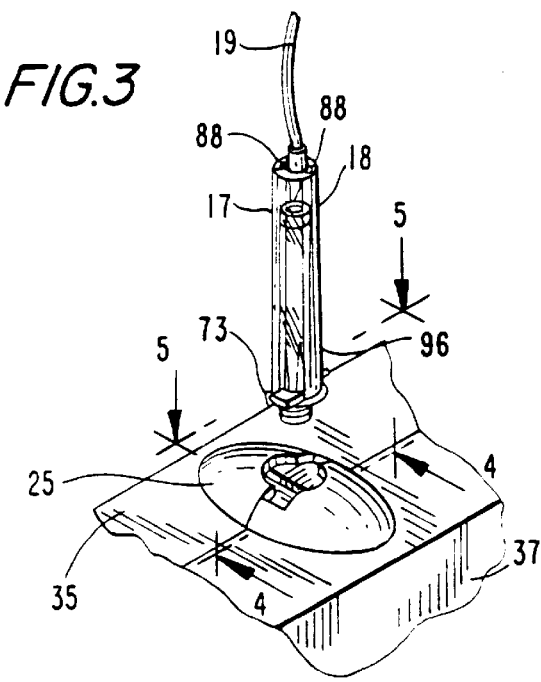
FIG.3
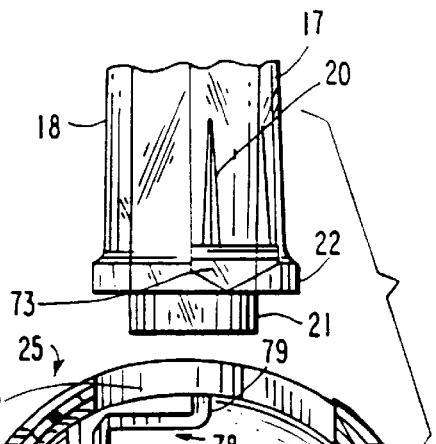
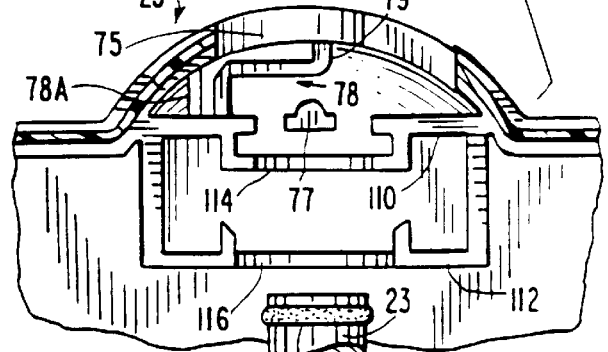
FIG.4
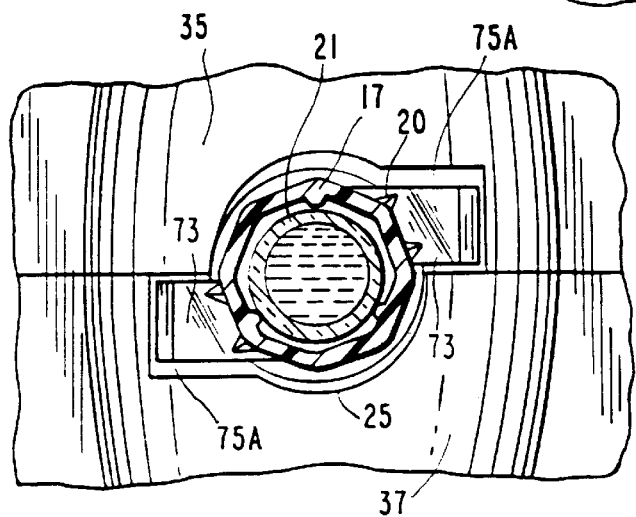
FIG.5

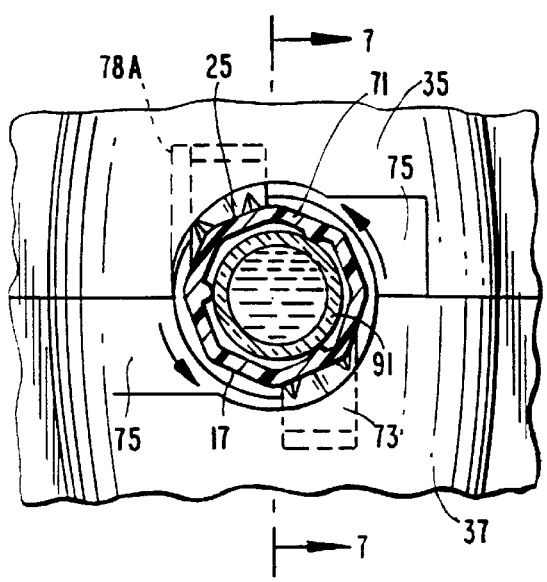
FIG.6
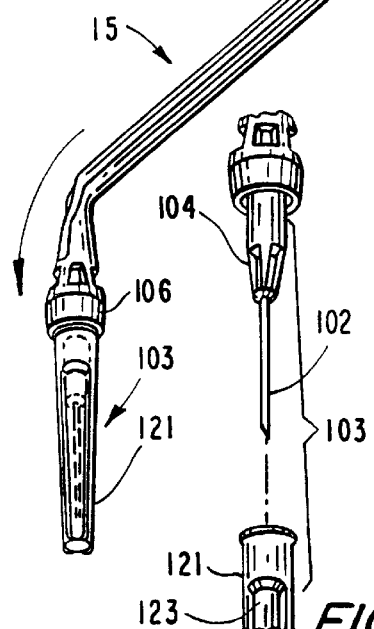
FIG.8
FIG.8A
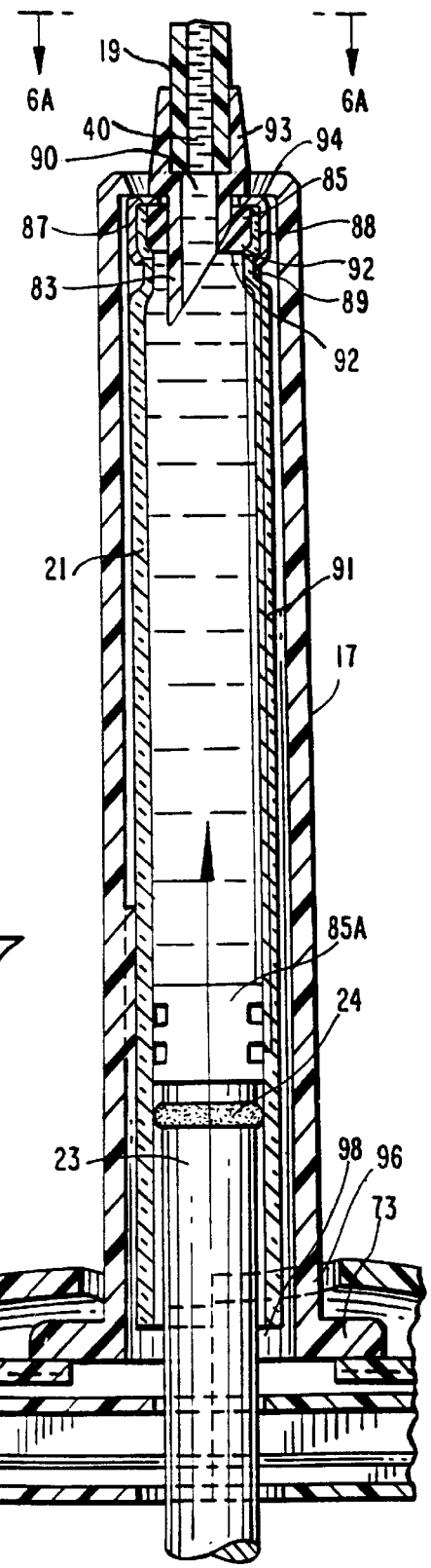
FIG.7

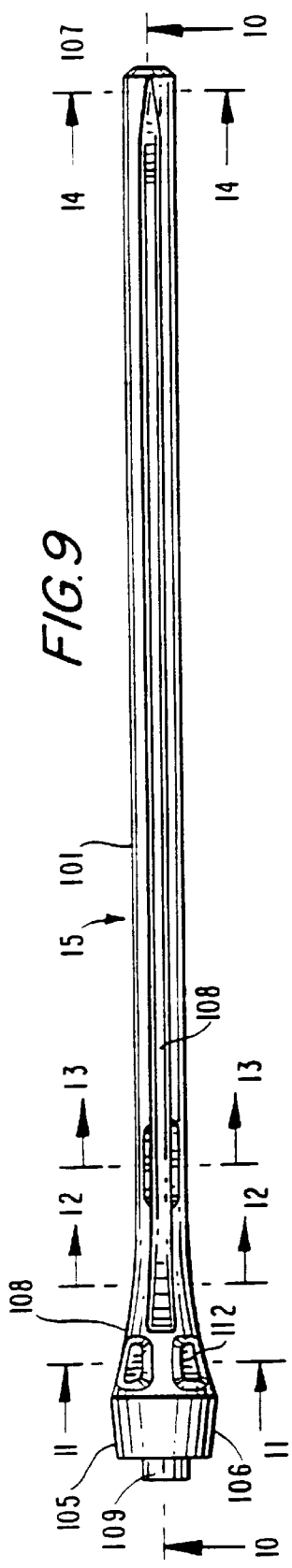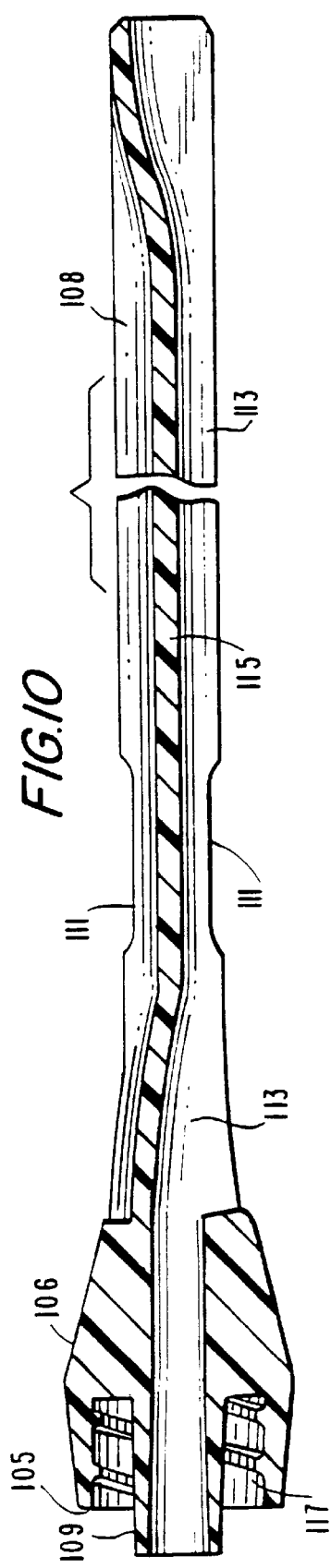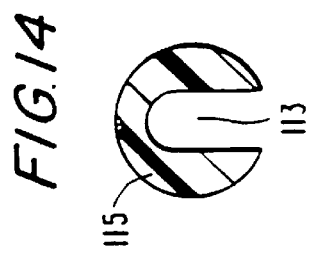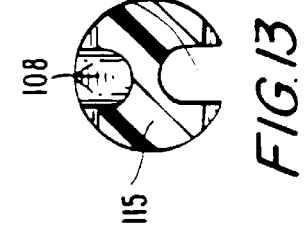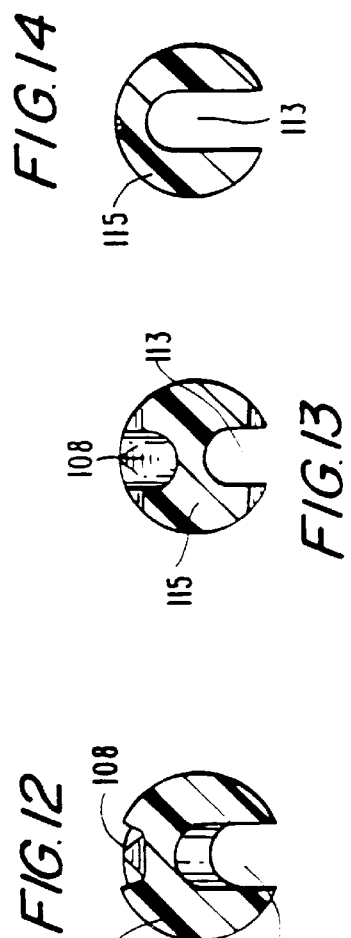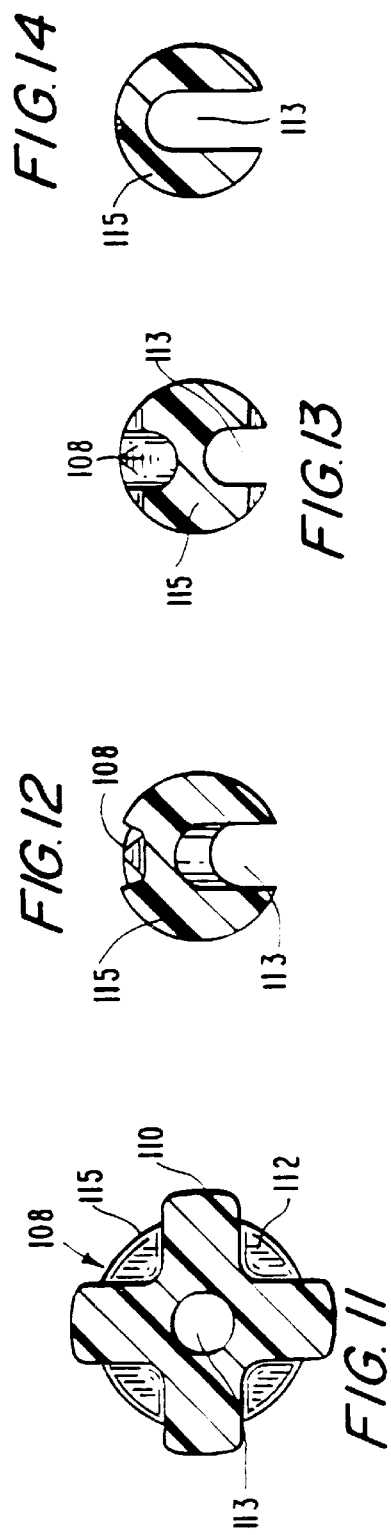

6,022,337

DENTAL ANESTHETIC AND DELIVERY INJECTION UNIT

This application claims benefit of Provisional application Ser. No. 80/057,531 filed Sep. 4, 1997.

BACKGROUND OF THE INVENTION

This application relates to a dental anesthetic injection delivery system, and more particularly to a system for injecting anesthetic safely and painlessly during a dental procedure.

While local anesthetics eliminate the often excruciating pain that would otherwise be suffered during dental extractions, drilling and reconstructions, the dental patient is still subject to pain from the hypodermic injection of the anesthetic into the local dental area of the mouth.

It is well established that more than 50% of adult patients fear injections in general, and even a greater number especially fear injections in the mouth during a dental procedure.

Accordingly, it would be desirable to provide a dental anesthetic injection delivery system which substantially eliminates the pain suffered by a patient during injection of anesthetic into the gum or other dental tissue.

SUMMARY OF THE INVENTION

Generally speaking, in accordance with the invention, there is provided a dental anesthetic delivery system which renders the nerve bundles which supply the teeth and supporting dental structures disabled in the area of the injection and in the path of the needle before a pain sensation is perceived by the dental patient. The system comprises a drive unit for selectively delivering anesthetic through a controllable handpiece unit which carries a needle for tissue penetration. Operation of the drive unit can be selectively controlled so that different amounts of anesthesia may be delivered through the needle, depending upon whether the dental practitioner is either penetrating the dental tissue or has otherwise reached the location within the mouth tissue where nerve disability is required.

The inventive system uses a linear activator to deliver a controlled amount of anesthetic from a cartridge that is locked into the drive unit. The drive unit is operated by a foot pedal which is selectively depressed in order to deliver anesthetic through the handpiece unit.

The system of the invention may be used to administer any liquid into the dental tissue, and is designed to accommodate a local anesthetic cartridge and a variety of needle sizes. The drive unit of the system includes a motor and an on-board microprocessor to facilitate control of anesthetic flow. The drive unit, utilizing the technology described in U.S. Pat. Nos. 4,747,824 and 5,180,371, and incorporated herein by reference, enables delivery of an anesthetic solution at a constant pressure and volume, regardless of variations in tissue resistance. At the delivery end of the needle, the system delivers a minute amount of the anesthetic which precedes the needle during injection in the dental tissue, creating in effect an anesthetic pathway. The combination of an anesthetic pathway and controlled pressure and volume (flow rate) results in an effective and pain-free injection.

The handpiece assembly, which carries the delivery needle, enables an unprecedented level of visibility and fingertip control. The handpiece assembly is linked to the selected anesthetic cartridge by plastic microtubing. The drive unit controls the reciprocating movement of a plunger which selectively and controllably dispenses anesthetic from the anesthetic cartridge and through the handpiece assembly in a predetermined flow profile.

Accordingly, it is an object of the invention to provide a dental anesthetic delivery injection system which can be used for most known dental injection procedures.

Yet another object of the invention is to provide a dental anesthetic delivery injection system which affords the dentist acute tactile response during operation.

A further object of the invention is to provide a dental anesthetic delivery injection system which selectively controls the amount of anesthetic being delivered through the dental procedure.

Yet another object of the invention is to provide a dental anesthetic injection delivery system which enhances the precision and accuracy of anesthetic delivery.

Still other objects and advantages of the invention will in part be obvious, and will in part be apparent from the following description.

BRIEF DESCRIPTION OF THE DRAWINGS

For a fuller understanding of the invention, reference is made to the following description, taken in connection with the accompanying drawings, in which:

FIG. 3 is a perspective view illustrating the placement of the selected anesthetic cartridge and cartridge holder of the inventive system in proper position on the drive unit in order to dispense anesthetic solution;

FIG. 4 is a side view, in partial cross-section, showing the cartridge holder disposed above a drive unit receptacle specially designed to accommodate the holder;

FIG. 5 is a top plan view, in partial cross-section, illustrating engagement of the cartridge holder in the receptacle of the drive unit;

FIG. 6 is a top plan view, in partial cross-section, similar to FIG. 5, in which the cartridge holder has been rotated within the drive unit receptacle in order to lock the holder and the retained anesthetic cartridge in place;

FIG. 6A details the forward end of the cartridge holder, taken along line 6A—6A in FIG. 7;

FIG. 7 is a cross-sectional view taken along line 7—7 of FIG. 6;

FIG. 8 is a perspective view of the handpiece unit of the inventive system, in which the handle thereof is shown in a bent condition in order to properly orient the needle during anesthetic injection;

FIG. 8A shows the needle cap being attached to or removed from the needle assembly of FIG. 8;

FIG. 9 is a side elevational view of the handle of the handpiece unit in an unbent condition;

FIG. 10 is a side view in cross-section of the handle depicted in FIG. 9 and illustrating in detail a tapered portion thereof along which the handle may be bent, as depicted in FIG. 8;

FIG. 11 is a cross-sectional view taken along line 11—11 of FIG. 10;

FIG. 12 is a cross-sectional view taken along line 12—12 of FIG. 9;

FIG. 13 is a cross-sectional view taken along line 13—13 of FIG. 9;

FIG. 14 is a cross-sectional view taken along line 14—14 of FIG. 9;

DETAILED DESCRIPTION OF THE PREFERRED EMBODIMENT

Figure 1:
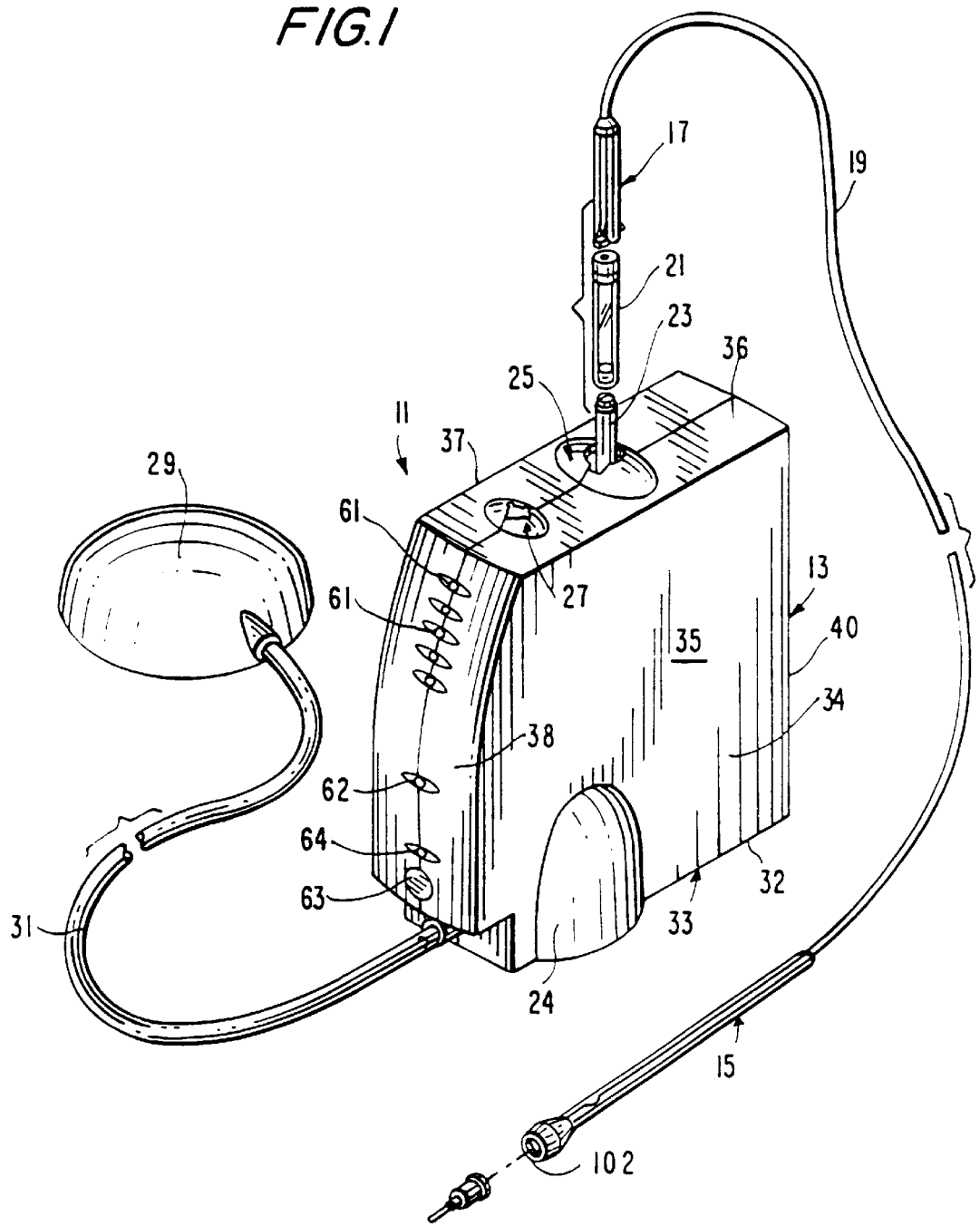
FIG. 1 is a perspective view of a dental anesthetic injection delivery system made in accordance with the invention.

Beginning with FIG. 1, a dental anesthetic injection delivery system, made in accordance with the invention, is described and generally indicated at 11. System 11 includes a drive unit, generally indicated at 13, a foot pedal 29 cooperatively connected to drive unit 13 by means of air hose 31, an anesthetic cartridge holder generally indicated at 17 for selectively retaining a cartridge 21 of a desired anesthetic, and a handpiece unit generally indicated at 15, cooperatively connected to anesthetic cartridge holder 17 by means of a predetermined length of microtubing 19.

Figure 2:
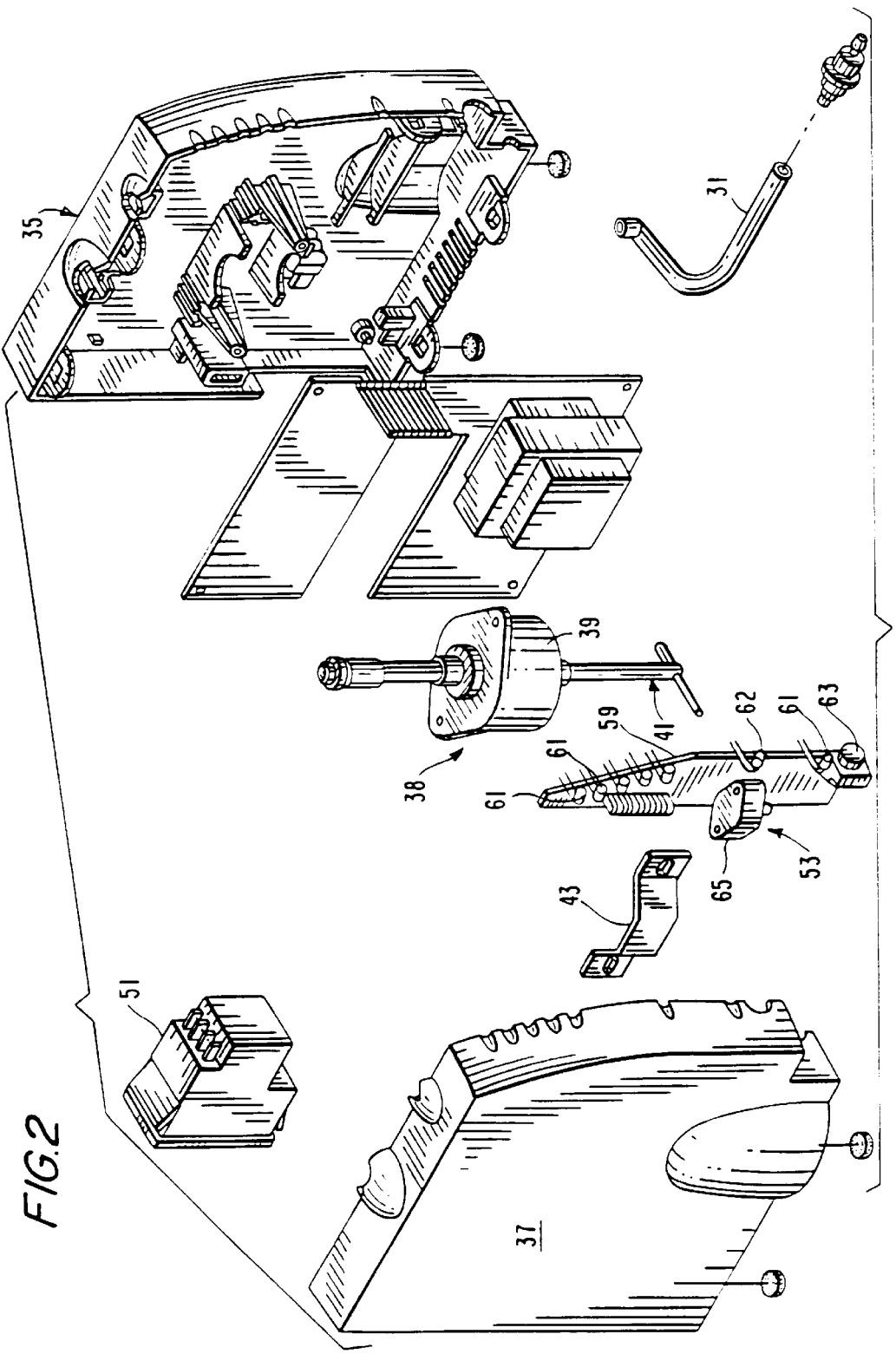
FIG. 2 is an exploded perspective view of the drive unit of the inventive dental anesthetic injection delivery system, and the component parts thereof.

Drive unit 13 comprises a substantially rectangular housing 33 having a bottom or base 32, sides 34, top 36 front portion 38, and rear portion 40. Housing 33 is defined by two mating and engageable halves 35 and 37, as best depicted in FIGS. 1 and 2. Housing 33 further includes a pair of lateral hubs 24 disposed on sides 34 of each housing half 35 and 37 along the bottom thereof to stabilize the drive unit 13 as it stands on a supporting surface.

Housing 33 of drive unit 13 includes a power switch 152 (shown in FIG. 19) along back portion 40 and a reset or aspirate with other controls, is selectively pressed in order to operate system 11 in three different modes of operation, as described hereinafter. Front portion 38 of housing 33 further includes a series of cartridge volume indicator lights 61, a power indicator light 62, and an aspirate indicator light 64, as shown in FIG. 1. Preferably lights 61, 62, 64 are LED's. Reset button 63 and lights 61, 62 and 64 are mounted on printed circuit board 59 installed inside unit 13 (see FIG. 2). As described in more detail below, power indicator light 62 is illuminated when the power switch is turned on; aspirate indicator light 64 is illuminated when the reset button 63 has been pressed and the aspirator function of the system is activated; and volume indicator lights 61 are selectively illuminated in order to show the volume of anesthetic solution remaining in cartridge 21 during operation of system 11.

Continuing now with FIG. 1, foot pedal 29 is preferably a round air bellows-type device and functions as an air-activated control element for selectively controlling the operation of system 11. Foot pedal 29 is operatively connected to air hose 31, which in turn is coupled to a pressure sensor 64 located inside unit 13. In operation of system 11, the pressure change from pedal 29 is detected by the sensor 64. Sensor 64 then generates a corresponding control signal used to control the flow of the anesthetic solution. In the preferred embodiment, as described in more detail below, when foot pedal 29 is slightly or partially depressed, system 11 operates at a slow speed. When foot pedal 29 is firmly or fully depressed, system 11 operates at a fast speed.

Turning now to FIGS. 3–7, cartridge holder 17 of system 11 is now described. Cartridge holder 17 is used for holding anesthetic cartridge 21 in proper engaged position in drive unit 13 in order to enable controlled dispensing of anesthetic solution to handpiece unit 15 for delivery therefrom. Cartridge holder 17 comprises an elongated plastic transparent cylindrical tube 71 having a forward end 94 and a rear end 96, as best shown in FIG. 7. Forward end 94 includes an outwardly projecting delivery sleeve 93 and an inwardly projecting protrusion or spike 83, both of which serve to define an exit pathway 90 or lumen through end 94 of holder 17. Sleeve 93 is engaged to and mates with one end of microtubing 19. Spike 83 is preferably designed with a surface cut at an angle of about 30 degrees and is used to puncture a sealing diaphragm of anesthetic cartridge 21 when said cartridge 21 is loaded into holder 17, as described below.

Rear end 96 of cartridge holder 17 includes a pair of opposite radially projecting wings 73, as shown in FIGS. 3 and 4. Wings 73 are used to engage and form an interference fit between end 96 of cartridge holder 17 and a receptacle 25 on housing 13. Preferably, receptacle 25 is formed along the top portion of housing 13, as best shown in FIGS. 1 and 3.

Cartridge holder receptacle 25, as best seen in FIGS. 3–5, is formed with a generally round opening 75 having a pair of oppositely disposed keyways 75A that are sized for receiving and accommodating wings 73 of cartridge holder 17 (see FIG. 5). Receptacle 25 further includes a pair of tongues 77 formed on each half 35 and 37 of housing 33 below keyways 75A, as well as a pair of corresponding cam members 79 disposed above each tongue 77. Each set of corresponding tongues 77 and cam members 79 define a locking slot 78 therebetween, as shown in FIG. 4.

Referring now to FIG. 6A, the forward end of holder 17 is provided with a plurality of holes 88. These holes can be used to assist in the removal of spent cartridges 21, as discussed below. Between these holes, there are provided a plurality of radial ribs 92 disposed inside the holder 17 used to stabilize cartridge 17 after said cartridge is fully inserted into the holder 17, in the position depicted in FIG. 7.

Turning once again to FIG. 7, the introduction and use of a typical anesthetic cartridge 21 is now described. Anesthetic cartridge 21 comprises a plastic or glass tube 91 defining an inside storage chamber 22 containing a desired anesthetic. Tube 91 has a forward portion 92 and a rear portion 98. Forward portion 92 is formed with a neck region 89 and an extending mouth 88 in which is fitted a diaphragm 85 adapted to be maintained in position within mouth 88 by means of a cap 87. Rear portion 98 has an end wall 85A which acts as a piston to express the anesthetic from the cartridge 21, in conjunction with plunger 23.

In order to load anesthetic cartridge 21 into holder 17, forward portion 92 of cartridge 21 is inserted through rear end 96 of holder 17 until approximately ¼ inch of cartridge 21 extends below end 96 of holder 17. Then, rear portion 98 of cartridge 21 and, more particularly, end wall 85A, is in contact with plunger 23 of unit 13, which is able to selectively pass through receptacle 25 during operation of system 11. Once plunger 23 is properly aligned with respect to cartridge 21, end 96 of holder 17 is seated within holder receptacle 25, as shown in FIG. 5, such that wings 73 are disposed within corresponding keyway 75.

In order to lock holder 17 within receptacle 25, end 96 of holder 17 is rotated one quarter turn in a counter-clockwise direction (see FIG. 6) such that each of wings 73 passes through or snaps a locking slot 78 and between corresponding tongue 77 and cam member 79. The plunger 23 is secured to motor 39 by standard right-handed threads (not shown). Therefore, as the receptacle 25 is secured in the counter-clockwise direction, it does not cause the plunger 23 to loosen. The distance between each tongue 77 and cam member 79 is slightly smaller than the thickness of wings 73. As each wing 73 turns and goes through one of the slots 78, respective tongue 77 flexes slightly downward. Once wing 73 goes through slot 78, tongue 77 snaps back, thereby locking the respective wing 73 in place. The rotation of holder 17 is terminated when wings 73 hit stops 78A.

Preferably, receptacle 25 with its opening 75, keyways 75A, tongues 77, cam members 79 and stops 78A are formed within a domed portion 26 of top 36 as shown. The bottom of receptacle 25 is defined by transverse walls 110, 112. Walls 110, 112 have corresponding holes 114, 116 coaxial with opening 75 which allow piston 23 to reciprocate in and out of housing 13, as described more fully below.

Significantly, during the loading of anesthetic cartridge 21 into drive unit 11, as described above, it is urged forward toward end 94 and as a result, spike 83 of holder 17 punctures diaphragm 85 of cartridge 21. This action provides a pathway or lumen between inside chamber 22 of cartridge 21 and exit pathway 90 of holder 17 so that anesthetic may flow through microtubing 19 and to handpiece unit 15 (see FIG. 8). Preferably, holder 17 has an outer surface 18 which is not cylindrical but polygonal, as best seen in FIG. 5. Surface 18 may have, for example, eight sides, i.e., it is octagonal in cross section. At the rear end 96 of holder 17, surface 18 is provided with a plurality of axial ribs 20 extending forwardly, which to facilitate engaging and disengaging holder 17 from housing 13. The octagonal shape of holder 17 is provided to facilitate the handling of the holder by the dentist or dental assistant, especially when he or she is wearing gloves.

Referring now to FIGS. 8–14, handpiece unit 15 is now further described. Handpiece unit 15 comprises a co-extruded handle member 101 of a substantially elongated design and a needle assembly 103 selectively engaged to one end of handle member 101. Handle member 101, as shown in FIGS. 9 and 10, is defined by a body 115 and has a forward bulbous end or head 105 and a rear end 107. End 105 is formed with an inwardly disposed Luer thread 113 and an extending plug 109, both of which are used for selectively engaging needle assembly 103, as shown in FIGS. 1 and 8.

Body 115 of handle member 101 defines a U-shaped elongated pathway or trough 113 in which microtubing 19 is selectively seated starting at forward end 105 and ending at rear end 107 (see FIGS. 9 and 10). During assembly, one end of microtubing 19 is first threaded into plug 109 of end 105, after which the rest of tubing 19 is press fitted into pathway 113. A solvent such as MEK (methylethyl ketone) is then used to permanently bond microtubing 19 in place.

Body 115 of handle member 101 further includes a longitudinal slot 108, which cooperates with pathway 113 to enhance a user's ability to grasp handle member 101.

Significantly, handle 101 is formed with a pair of cut-outs 111 adjacent forward end 105 in order to define a tapered weak zone in body 115. As a result, and as best depicted in FIG. 8, handle 101 may be flexed (with some modest effort) and plastically deformed at the location of cut-outs 111 in order to properly orient needle assembly 103 during operation of system 11.

Figure 15:
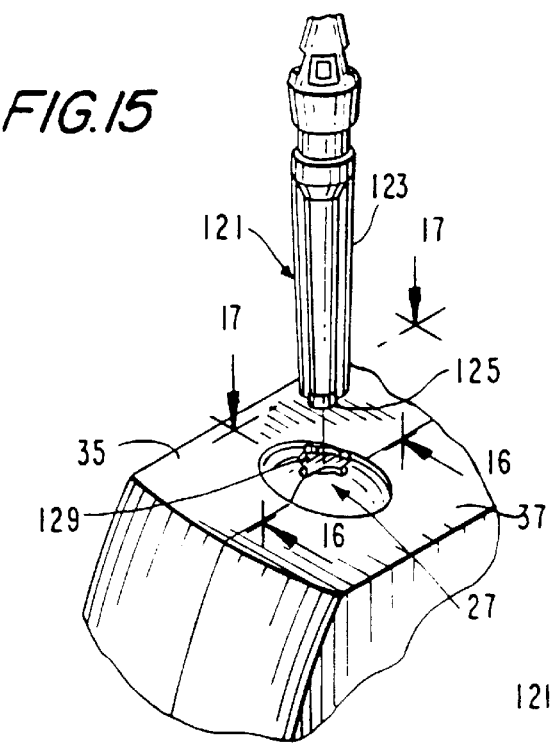
FIG. 15 is a perspective view illustrating one embodiment of the needle assembly of the handpiece unit as it is being placed in a specially designed storage receptacle of the drive unit.
Figure 16:
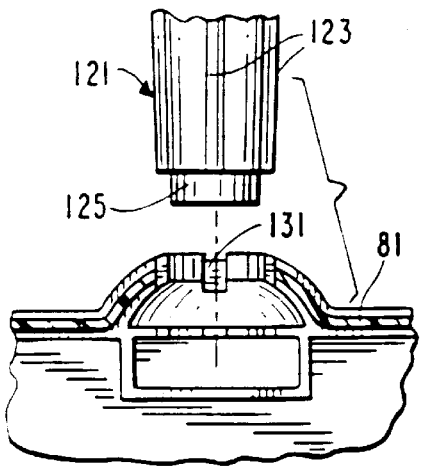
FIG. 16 is side elevational view, in partial cross-section, showing in greater detail the placement of the needle assembly in the drive unit receptacle.

Turning to a consideration of FIGS. 8A, 15 and 16, needle assembly 103 is now further described. Needle assembly 103 includes a needle cover 121 having a series of longitudinally extending ribs 123 formed along the outside surface thereof and a Luer lock needle 102. Needle cover 121 has a forward end 125 designed for selective reception by handpiece receptacle 27 formed along top 36 of drive unit 13, and a rear end for selectively engaging with end 105 of handle member 101, thereby covering of needle needle 102, which is permanently attached to sleeve 104 (FIG. 8A). Sleeve 104 is in turn coupled to head 105 by the Luer connection.

Handpiece receptacle 27 of drive unit 11 is designed to hold needle cover 121 firmly in place for storage while handpiece 15 is in use, i.e., when the cover 121 is removed from the handle member 101. It is also designed to store cover 121 with needle assembly 103 captured therein until the user is ready to operate system 11.

Figure 17:
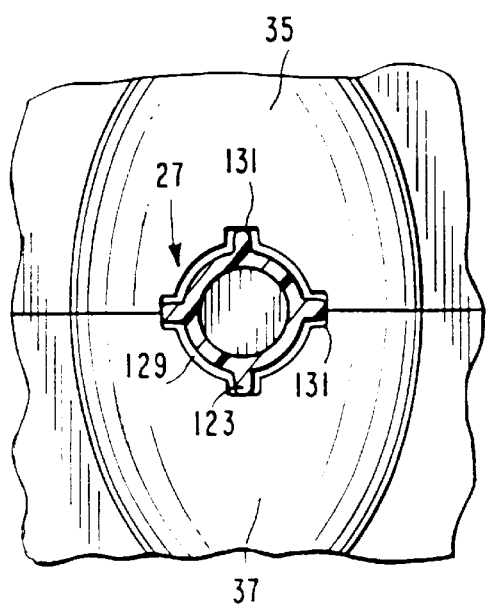
FIG. 17 is a top view, in partial cross-section, showing final engagement of the needle assembly in the drive unit receptacle, said needle assembly having a first configuration.

Handpiece receptacle 27 is defined by an annular opening 129 having along the circumference thereof four outwardly formed arcuate projections 131. In order to secure needle cover 121 in receptacle 27, cover 125 is placed in opening 129 such that ribs 123 are received within projections 131, as best shown in FIG. 17.

Figure 18:
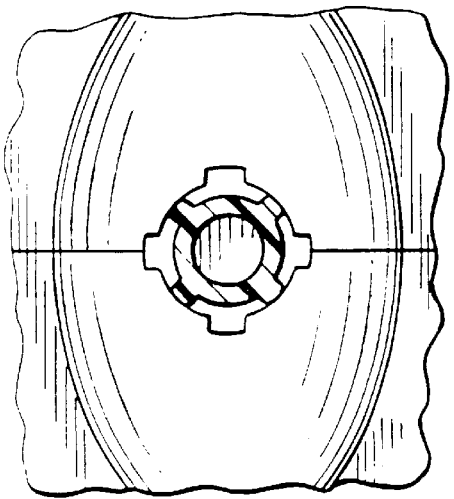
FIG. 18 is similar to FIG. 17, but illustrating the engagement of a needle assembly in the drive unit receptacle, said needle assembly having a second configuration.

Of course, the size of the needle and its cover may change. If needle cover 121 is of a smaller size, then its ribs are simply held tightly along the ring defined by opening 129 (see FIG. 18). Thus, receptacle 27 is adapted to accommodate needle assemblies of various sizes.

Figure 19:
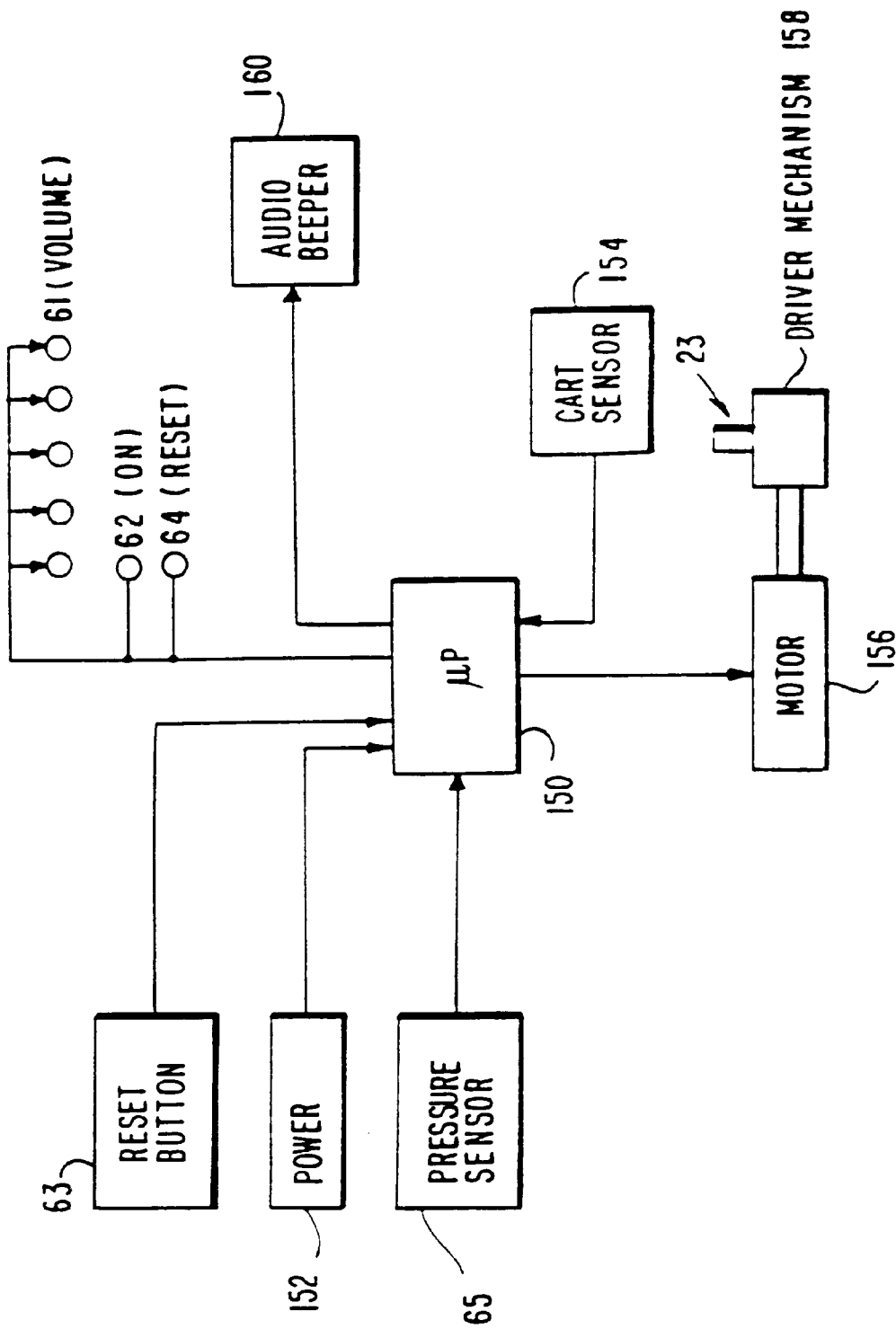
FIG. 19 shows a block diagram for the various electrical elements of the system.

The entire system 11 is powered electrically, with various actions occurring under the control of an operator who activates the appropriate control functions of the system. To illustrate how this is achieved, FIG. 19 shows a schematic diagram of the various electrical elements of the system. These elements combine to define the control circuit of the system. The system includes a microprocessor 150. This microprocessor 150 receives inputs from the power switch 152, pressure sensor 65, reset button 63 and a cartridge sensor 154 used to sense when the cartridge 21 is in place as discussed above. The microprocessor 150, in response to the signals received from these input members, activates lights 61, 62 and 64, as well as an audio beeper 160, as discussed below. The microprocessor 150 further operates a motor 156. The motor activates a driver mechanism 158 used to reciprocate plunger 23.

Figure 20:
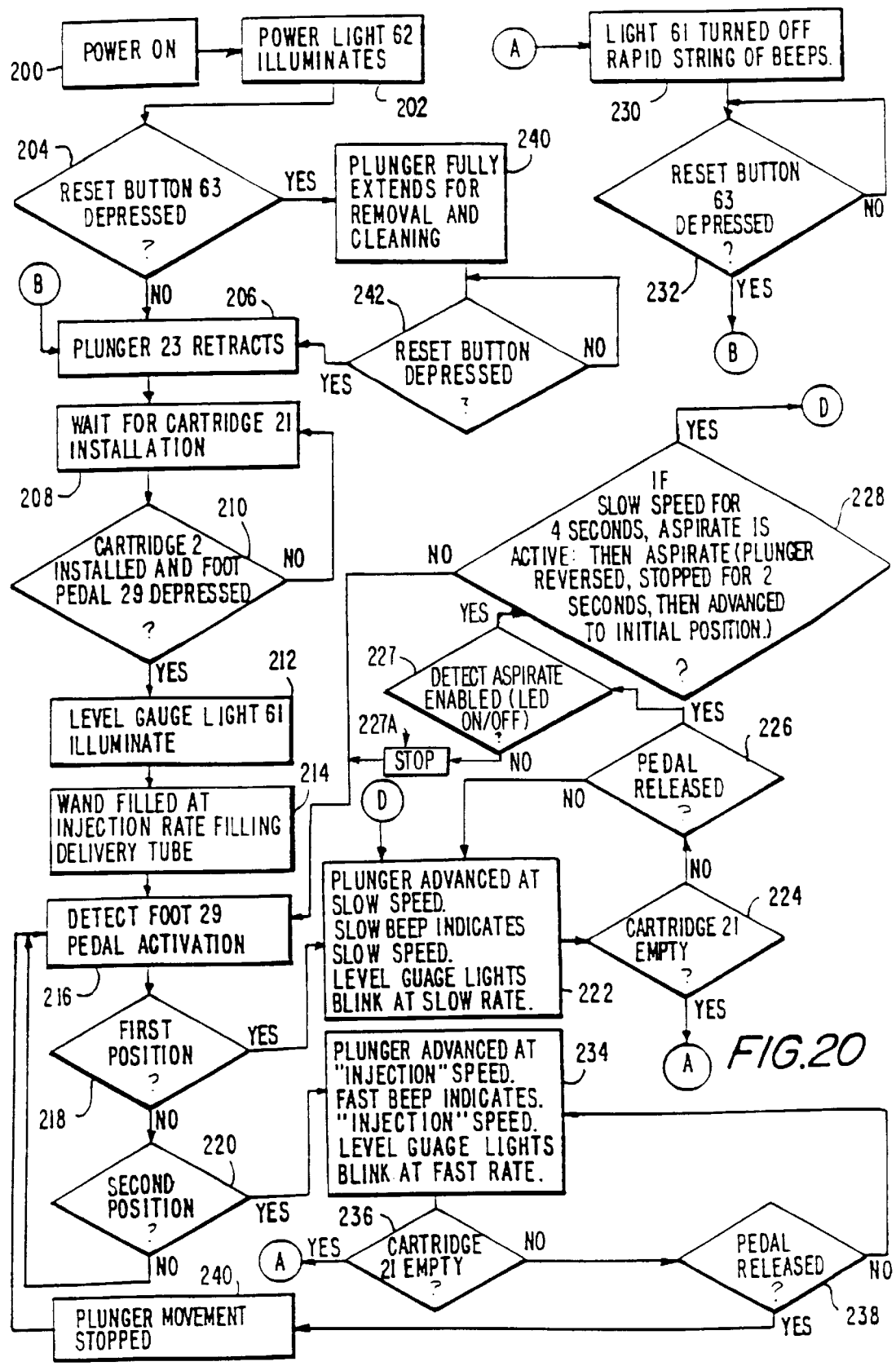
FIG. 20 shows a flow chart illustrating the operational sequence of the delivery system of FIGS. 1–18.

The sequential operation of the subject injection device is illustrated by the flow chart of FIG. 20. Starting with step 200, the power for the injection device is turned on by activating switch 152. In step 202 the power indicator light 62 is turned on, followed by step 204 when a check is performed to determine if the reset button 63 is pressed. If not, then in step 206 the plunger 23 is retracted into the housing 13 and the device waits for a cartridge 21 to be installed.

In step 210, a check is performed to determine if cartridge 21 has been installed via sensor 154 and if foot pedal 29 has been depressed. If both these conditions are met then in step 212, lights 61 are activated. Initially, since the cartridge 21 is full, all the lights 61 are on. As the process of dispensing the anesthetic solution continues, the microprocessor keeps a running count of how much of the solution has been expressed from the cartridge by the position of the plunger 23 and activates the indicator lights 61 to show the remaining volume.

After step 212, in step 214, the plunger 23 is advanced so that it comes in contact with, and in effect, interlocks with, the rear end 85A of cartridge 21 in a manner well known in the art of syringes. Therefore, as the plunger reciprocates, it moves end 85A, which acts as a piston as previously discussed. The plunger continues to advance by a predetermined amount at a low injection rate. The plunger is advanced until sufficient solution has been expressed from the cartridge 21 to fill the microtube 19 and needle 102. In this manner, the system is automatically purged of any air bubbles.

In step 216, the pedal 29 is again checked to see if it is still activated. More specifically, in step 218, a check is performed to determine if the pedal 29 is in its first position. If it is not, then in step 220 a check is performed to determine if the pedal 29 is in its second position. If the pedal is not in the first or the second position, then it is inactive and the system waits for the pedal to be activated again (step 216).

If in step 218 it is determined that the pedal 29 is in the first position, then in step 222, a slow delivery subroutine is initiated. During this subroutine, the plunger 29 is advanced slowly, beeper 160 (controlled by the microprocessor 150) beeps at a first, relatively low rate, and the lights 61 are all blinking at a low rate as well, for example in synchronism with the beep. As part of this subroutine in step 224, a check is performed to determine if the cartridge 21 is empty yet. If it is not, then in step 226, the pedal is checked to see if it has been released. If the pedal 29 is not released, then the plunger 23 continues advancing at slow rate (step 222).

If the pedal 29 is released, then in step 227 a check is performed to see if the aspirate function has been enabled via batten 63. If it has then the LED 64 is turned on and the process continues to step 228. If the aspirate mode has not been enabled, then in step 227A the plunger is stopped and the process continues to step 216 to wait for the next activation of pedal 29.

In step 228 a check is performed to determine if the slow delivery has been activated for a predetermined time duration, for example four seconds. After four seconds of slow delivery, during step 228, the reset button 63 is checked to see, in this case, if the user has requested aspiration. Thus, the user can request an aspiration after four seconds of slow delivery. If the user has requested aspiration, then the plunger 23 is reversed for a predetermined distance, stops for a programmable time period (for example, 2 seconds) and then advances back to its original position (i.e., to the position of the plunger at the moment when the reset button was depressed). Thereafter, the device goes back to step 216 and waits for the activation of the pedal 29.

Going back to step 224, the cartridge 21 becomes empty, as determined by the microprocessor, then in step 230 all the lights 61 are deactivated and a rapid series of beeps is issued by beeper 160. During these beeps, step 232 requires a check to be performed to determine if the reset button 63 has been depressed. When the button 63 is depressed, the device returns to step 206 where the plunger 23 retracts and the device is ready for a fresh cartridge 21.

An alternate sequence starts with step 220 if the pedal 29 is found to be in the second position, causing a fast delivery subroutine is initiated. More specifically, in step 234, the plunger is advanced at faster rate, and, simultaneously, the lights 61 and the beeper are activated at a higher rate than in step 222. For example, at the slower rate, the device may deliver anesthetic at 1 drop/sec. (or typically about 0.02 ml/sec.), while at the faster rate, the anesthetic may be delivered at 0.04 ml/sec.

Meanwhile, in step 236, a check is performed to determine if the cartridge 21 is empty. If it is, then steps 230 and 232 are performed as discussed above. But if cartridge 21 is not empty, then in step 238 a test is performed to determine if the pedal 29 has been released. If the pedal is released, then the device returns to step 216 and waits for a pedal activation; however, if the pedal is not released (step 238), then the higher speed anesthetic delivery continues.

Returning to early step 204, if the reset button 63 was depressed at the same time as the power button, then a cleaning subroutine is initiated. As part of this subroutine, the plunger 23 is fully extended and remains in that position so that it can be cleaned and/or replaced. When the reset button 63 is depressed (as determined in step 242) the plunger retracts (step 206) and normal operation resumes.

In summary, reset button 63, pedal 29 and switch 152 of drive unit 13 are used to define three different modes of operation of system 11. In the first mode of operation, when reset button 63 is held down continuously for about two seconds, plunger 23 is fully retracted into the inside of drive unit 13 ("home" position).

In the second mode of operation, the reset button is pressed and then foot pedal 29 is slightly depressed and held for four audible beeps and then removed. This activates the aspirating mode of system 11, as described.

In the third mode of operation, when reset button 63 is pressed and held down, and when switch 152 is activated, the cleaning of system 11 is initiated and plunger 23 is fully extended for easy removal in order to clean or replace it.

In order to remove cartridge 21 from drive unit 13 after use, cartridge holder 17 is first released from receptacle 25 by rotating end 96 an opposite quarter turn. Then, the operator places the tip of a suitable pointed instrument into holes 88 (see FIG. 6A) formed along forward end 94 of cartridge holder 17 in order to push cartridge 17 out of holder 17.

Now that the elements and components of the subject invention has been described in great detail, a typical operation is provided for a better understanding of its advantages. The system is initialized when the power button is turned on. Once the power is on, the plunger 23 retracts to a 'home' position and the power light 62 goes on. The dentist or dental assistant then inserts a cartridge 21 into the cartridge holder 17 and positions the head of the plunger 23 into the bottom of the cartridge holder 17 so that this head abuts the piston 85A. The cartridge holder is then secured to the housing 13 by pressing it down into receptacle 25 and twisting it clockwise by about 90° (see FIGS. 1, 3–6). This motion also forces the cartridge holder 17 to slide over the piston 23. This motion in turn causes the spike 83 to move downward and break the seal 92, thereby opening the cartridge 21. Thus, in one movement, the cartridge holder 17 is mounted onto housing 13 and, at the same time, the cartridge 21 is unsealed. Next, the foot pedal 29 is depressed once, causing the piston 23 to advance upward by a predetermined amount thereby forcing the anesthetic from cartridge 21 to flood the microtube 19 through the handle 15 to needle 102 until a small amount squirts out. In this manner, air is purged from the microtube 19 and needle 102. After this automatic purging, the lights 61 go on, indicating that the cartridge is full and that the whole system is now ready for operation.

In order to start infusing the aesthetic, the dentist first takes the handle 15, removes the cap 121 and inserts the needle 102 into the appropriate tissue. Advantageously, the cap 121 can be stored in receptacle 27. If necessary, the dentist may bend the handle 15 as shown in FIG. 8. Dispensing of the anesthetic is started by pushing down and holding foot pedal 29 in the first position which causes the plunger 23 to move upward at a constant first rate. As long as the foot pedal 29 is held in the first position, a steady beep is emitted at about 1 second intervals and the level gauge lights 61 blink at the same rate. If the dentist wants to dispense the anesthetic at the faster rate, he pushed down on the pedal 29 to the second position. The plunger 23 then moves faster. This mode of operation is indicated by the lights 61 blinking faster, and the beeper 160 emitting sounds at a faster rate as well. To stop the anesthetic dispensing, the dentist removes his foot from the pedal 29. This action causes the plunger 23 to stop. The lights 61 stop blinking and stay on and the beeper 160 stops emitting beeps as well. Before going on to other procedures, the dentist installs the cap 121 on the needle 102 and then rests the handle 15 over receptacle 27 with the cap 121 extending into the receptacle 27.

As the anesthetic is being dispensed, the position of the plunger 23 is contiguously monitored to determine the amount of anesthetic left in cartridge 21. When the cartridge 21 becomes empty, the plunger 23 stops, the lights 61 go off and a series of rapid beeps are emitted by beeper 160 to indicate that the cartridge 21 needs to be replaced.

If aspiration is desired, the dentist first operates the foot pedal in the first position for at least four seconds (i.e., four beeps). He then activates the reset/aspirate button 63. This action causes light 64 to go on and the plunger 23 to reverse its forward movement for a predetermined distance thereby causing anesthetic (and, occasionally, body fluids) to be withdrawn into the microtube 21. After moving back, the plunger 23 stops for two seconds (to allow the dentist to visually inspect the contents of the microtube 19 within the handle 15) and then advances back to its original position. If the foot pedal 29 is still depressed, the plunger 23 then continues its forward movement.

At the end of a procedure, the dentist pushes button 63 for two seconds. This action causes the plunger 23 to return to its original position, thereby allowing the cartridge 21 to be removed and discarded.

Preferably, for a new patient, all the disposable elements of the system are discarded. This can be accomplished by turning the power button 152 and reset button 63 on simultaneously. These actions initiate the cleaning mode during which the plunger is fully extended so that it can be removed and discarded, together with the cartridge holder 17, microtube 19 and handle 15.

The system of the invention, under microprocessor control, delivers precise pressure and volume ratios of anesthetic. Even in resilient dental tissue, such as the palate and periodontal ligament, the inventive system delivers an anesthetic drip which precedes needle entry, effectively creating an anesthetic pathway. This combination of an anesthetic pathway and controlled flow rate results in a virtually imperceptible injection and rapid onset of profound anesthesia, all for the patient's comfort and relief.

In addition, the inventive system affords greater tactile control than traditional dental syringe units, and precise needle placement is therefore assured.

It will thus be seen that the objects set forth above, among those made apparent from the preceding description, are efficiently attained, and since changes may be made without departing from the spirit and scope of the invention, it is understood that the above description is merely illustrative and does not otherwise limit the scope of the invention. The claims that follow define the inventive scope.

We claim:
1. An injection device comprising:
   a housing having a pump disposed in said housing, said housing having thereon a first receptacle and a second receptacle; and
   a disposable delivery system for delivering a therapeutic agent to a patient, said delivery system including a supply end, a delivery end with a handle having a needle for selective injection of said agent into said patient and a flexible tube extending between said supply end and said delivery end;
   wherein said supply end is constructed and arranged to couple to said first receptacle, with said supply end and said pump cooperating to force said agent to flow from said supply end to said delivery end; said supply end including a cartridge holder adapted to house a cartridge for storing to store said agent.
2. The device of claim 1 wherein said pump includes a plunger and a controller reciprocating said plunger through said cartridge to control the flow of said therapeutic agent.
3. The device of claim 1 further comprising a quick disconnect coupler for coupling said supply end to said housing.
4. The device of claim 3 wherein said coupler includes a tongue disposed within said first receptacle and wherein said supply end has a wing, said supply end being rotatable between a first position in which said supply end is retractable from and insertable into said receptacle and a second position in which said wing and tongue form an interlock.
5. The device of claim 4 further comprising a plunger reciprocating within said first receptacle and wherein said tongue and wing cooperate to hold said supply end in said second position in axial alignment with said plunger.
6. An injection device comprising:
   a housing having a pump disposed in said housing, said housing having thereon a receptacle;
   a disposable delivery system for delivering a therapeutic agent to a patient, said delivery system including a supply end and a handle having a needle for selective injection of said agent into said patient, a flexible tube extending between said supply end and said handle, a cartridge holder associated with said supply end and a replaceable cartridge adapted to hold said agent, said cartridge being disposed in said cartridge holder; and
   a quick disconnect coupling member for selectively mounting and removing said supply end to and from said housing.
7. The device of claim 6 wherein said supply end is constructed and arranged to couple to said receptacle, with said supply end and said pump cooperating to force said agent to flow from said supply end to said syringe.
8. The device of claim 6 wherein said cartridge holder includes a forward end adapted to connect to said flexible tube and a rear end adapted to couple to said receptacle.
9. The device of claim 8 wherein said cartridge holder has an end wall, said end wall being provided with a stabilizing element for stabilizing said cartridge after said cartridge has been inserted into said cartridge holder.
10. The device of claim 8 wherein said cartridge holder has rear end and an outer surface, said outer surface being provided with a plurality of ribs extending longitudinally adjacent to said rear end, said ribs being provided to facilitate manipulating said cartridge holder along its longitudinal axis.
11. The device of claim 8 wherein said cartridge has a longitudinal axis and an outlet disposed at said forward end along said longitudinal axis.

12. The device of claim 11 further comprising a piercing member for piercing said diaphragm said piercing member being disposed at said forward end.

13. The device of claim 12 wherein said outlet and said piercing member define a lumen through which said agent is expressed.

14. The device of claim 8 wherein said cartridge holder has an end wall, said end wall being provided with access holes, said holes being adapted to receive an external tool for selectively removing said cartridge.

15. The device of claim 14 wherein said outer wall defines an octagon.

16. The device of claim 15 wherein said cartridge holder has an outer longitudinal wall, said outer longitudinal wall defining a cross-sectional polygon.

17. The device of claim 8 wherein said cartridge has a diaphragm which is adapted to seal said agent within said cartridge.

18. The device of claim 17 wherein said cartridge holder further including a piercing member for piercing said diaphragm when said cartridge is inserted into said cartridge holder.

19. The device of claim 18 wherein said piercing member is disposed at said forward end.

20. An injection system for delivering a therapeutic agent to a patient, said system comprising:
   a source of therapeutic agent;
   a delivery member adapted to deliver said agent to said patient;
   a pump for selectively pumping said agent from said source to said delivery member;
   an automatic controller for controlling said pump; and
   a control switching device to define a first and a second mode of operation for said controller;
   wherein in said first mode of operation said controller operates said pump to cause said agent to flow forward toward said patient; and
   wherein in said second mode of operation said controller operates said pump to cause said agent to flow backwards, away from said patient, said controller being constructed and arranged to enter into said second mode of operation only a predetermined time after said first mode of operation has been active.

21. The injection system of claim 20 further comprising a capacity indicator for indicating the amount of agent in said source, said capacity indicator being activated by said controller.

22. The injection system of claim 20 further comprising a visual mode indicator and a sounding device for indicating the mode of operation of said controller.

23. The injection system of claim 20 wherein said switching device includes a first switch and a second switch, said first and second switches cooperating to define said first and second modes.

24. The system of claim 20 further comprising a power switch for selectively providing power to said system.

25. The system of claim 24 wherein said switch member defines a third mode of operation for said controller, said third mode being provided for cleaning and maintenance said pump.

26. An injection system for delivering a therapeutic agent to a patient, said system comprising:
   a source of therapeutic agent;
   a delivery member adapted to deliver said agent to said patient;
   a pump for selectively pumping said agent from said source to said delivery member;
   an automatic controller for controlling said pump; and
   a control switch member for actuation by a user;
   wherein said control switch member has a first and a second position, and wherein, in response to said control switch member being in said first position, said controller operates said pump to deliver said agent at a first rate, and wherein, in response to said control switch member being in said second position, said controller operates said pump to deliver said agent at a second rate.

27. The system of claim 26 wherein said first switch is a foot switch.

28. The system of claim 27 wherein said foot switch is coupled to said controller by an air hose and where in said controller includes a pressure sensor.

29. The system of claim 28 wherein said pressure sensor generates a signal for said controller, said signal being indicative of the position of said foot switch.

30. The device of claim 26 further comprising a housing, said pump being disposed in said housing and having a plunger adapted to reciprocate in response to signals from said controller.

31. The device of claim 30 wherein said plunger has a first position in which the plunger is disposed in said housing and a second position in which the plunger is disposed outside said housing for easy removal and replacement.

32. An injection device comprising:
   a housing having thereon a receptacle;
   a pump; and
   a delivery system for delivering a therapeutic agent to a patient, said delivery system including a supply end, a delivery end with a handle having a needle for selective injection of said agent into said patient when said pump is activated, said needle being associated with a protective cover, and a flexible tube extending between said supply end and said delivery end;
   wherein said supply end is constructed and arranged to couple to said housing; and
   wherein said receptacle is constructed and arranged to receive said handle for storage by engaging said protective cover, with said handle being removable from said protective cover while said protective cover remains engaged by said receptacle.

33. The injection device of claim 32 wherein said receptacle and said cover form an interference fit.

34. An injection system for delivering a therapeutic agent to a patient, said system comprising:
   a source of therapeutic agent;
   a delivery member adapted to deliver said agent to said patient;
   a pump for selectively pumping said agent from said source to said delivery member;
   an automatic controller for controlling said pump; and
   a control switch member for actuation by a user to actuate said controller, said control switch member including a foot switch coupled to said controller by an air hose, said controller further including a pressure sensor that senses the activation of said foot switch.

35. An injection system for delivering a therapeutic agent to a patient, said system comprising:
   a source of therapeutic agent;
   a delivery member adapted to deliver said agent to said patient;

a pump for selectively pumping said agent from said source to said delivery member;

an automatic controller for controlling said pump; and a control switch member for actuation by a user to actuate said controller, said control switch defining a first mode of operation during which said controller operates said pump to infuse said agent, said control switch defining a second mode of operation, wherein in second mode of operation said controller operates to clean the system.

36. The injection system of claim 35 further comprising a piston associated with said pump and a housing containing said piston, wherein during said second mode of operation said controller causes said piston to extend out of said housing.

37. The injection system of claim 35 wherein said piston is disposable.

* * * * *